United States Patent
Schweinfurth et al.

(10) Patent No.: US 12,374,447 B1
(45) Date of Patent: Jul. 29, 2025

(54) CAREGIVER/CAREGIVEE MOBILE APPLICATION MANAGEMENT

(71) Applicant: WALGREEN CO., Deerfield, IL (US)

(72) Inventors: Andrew David Schweinfurth, Chicago, IL (US); Julija Alegra Petkus, Oak Park, IL (US)

(73) Assignee: WALGREEN CO., Deerfield, IL (US)

( * ) Notice: Subject to any disclaimer, the term of this patent is extended or adjusted under 35 U.S.C. 154(b) by 336 days.

(21) Appl. No.: 17/523,756

(22) Filed: Nov. 10, 2021

(51) Int. Cl.
*G16H 40/40* (2018.01)
*G16H 20/10* (2018.01)

(52) U.S. Cl.
CPC .............. *G16H 40/40* (2018.01); *G16H 20/10* (2018.01)

(58) Field of Classification Search
CPC ................................ G16H 20/10; G16H 40/40
USPC ............................................................ 705/2
See application file for complete search history.

(56) References Cited

U.S. PATENT DOCUMENTS

| | | | |
|---|---|---|---|
| 7,808,391 B2 | 10/2010 | Nixon | |
| 9,572,748 B2 | 2/2017 | Lim et al. | |
| 11,152,091 B1* | 10/2021 | Makarskyy | G06Q 50/22 |
| 2011/0125528 A1* | 5/2011 | Padate | G16H 10/60 705/3 |
| 2013/0065569 A1* | 3/2013 | Leipzig | H04W 4/16 455/420 |
| 2017/0364637 A1* | 12/2017 | Kshepakaran | G16H 10/60 |

FOREIGN PATENT DOCUMENTS

CA 3119570 A1 * 11/2021 ......... G06F 21/6254

OTHER PUBLICATIONS

CareZone, Retrieved from the internet at: <URL:https://carezone.com/> (2021).
Walmart Wellness Google App, Retrieved from the internet at: <URL:https://play.google.com/store/apps/details?id=com.walmart.caredroid&hl=en_US&gl-US> (2021).
MediSafe, Retrieved from the internet at: <URL:https://www.medisafeapp.com/> (2021).
MedMinder, Retrieved from the internet at: <URL:https://www.medminder.com/> (2021).
(Continued)

Primary Examiner — Hiep V Nguyen
(74) Attorney, Agent, or Firm — MARSHALL, GERSTEIN & BORUN LLP; Randall G. Rueth

(57) ABSTRACT

An example computer-implemented method includes: receiving, via a first instance of an application at a first computing device, a request from a first user account for caregiver access to a second user account; verifying that the first user account is authorized by the second user account to receive the caregiver access; responsive to the verifying, retrieving (i) account data of the second user account including prescription information indicating a prescription of the second user, and (ii) an application configuration including settings of the application for the second user account, the settings including notification settings for the prescription; providing the first user account with the caregiver access by providing access to the account data and the application configuration via the first instance of the application; receiving, from the first computing device, an update to the application configuration; and modifying the application configuration in accordance with the update.

13 Claims, 5 Drawing Sheets

(56) References Cited

OTHER PUBLICATIONS

PillPack by Amazon Pharmacy Help Center—Creating a caregiver account, Retrieved from the internet at: <URL:https://help.pillpack.com/hc/en-us/articles/360002096028-Creating-a-caregiver-account> (2021).

Google Family Link for parents Google App, Retrieved from the internet at: <URL:https://play.google.com/store/apps/details?id=com.google.android.apps.kids.familylink&hl=en_US&gl=US> (2021).

* cited by examiner

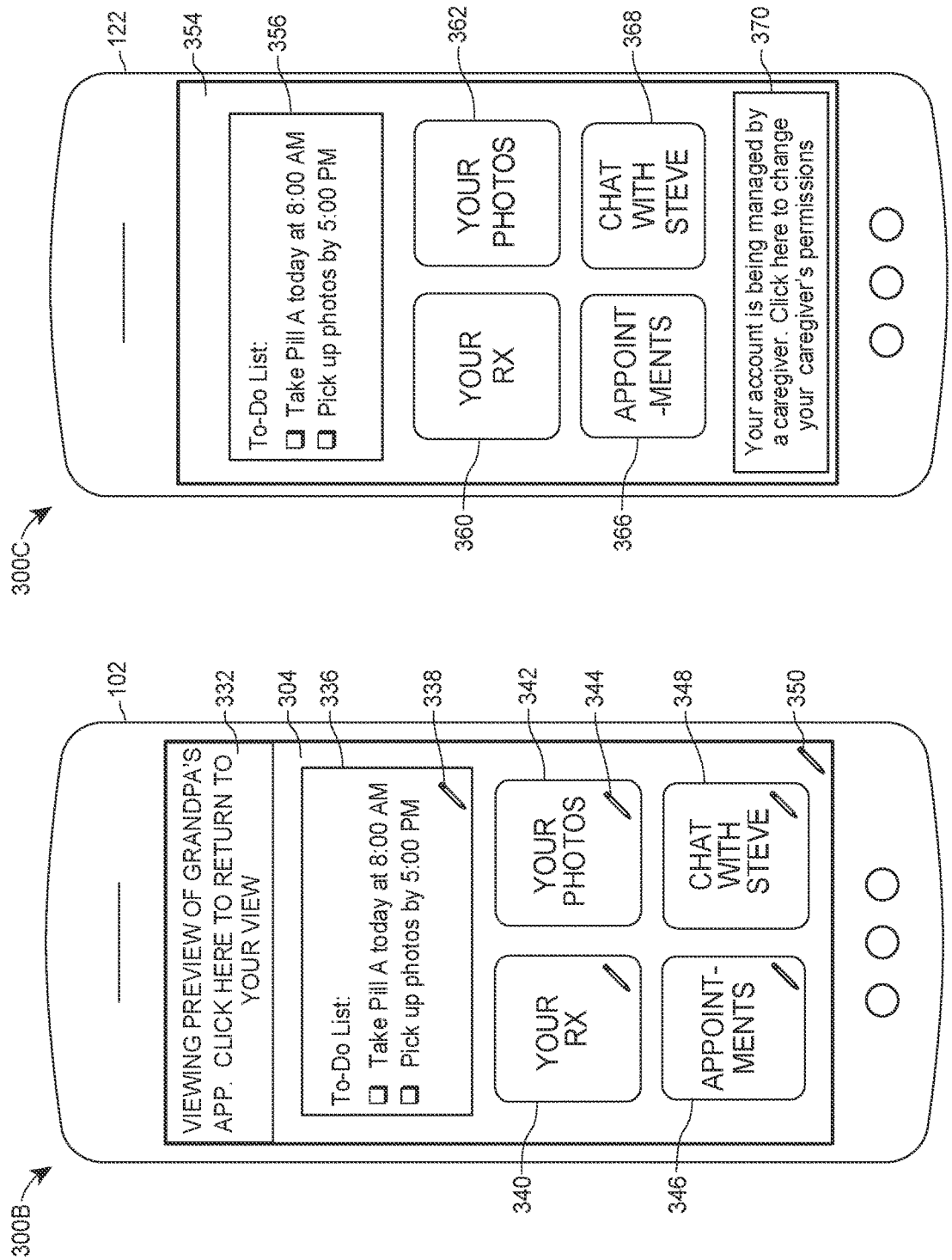

CAREGIVER/CAREGIVEE MOBILE APPLICATION MANAGEMENT

FIELD OF THE DISCLOSURE

The present disclosure generally relates to application management and, more particularly, to computer-implemented methods and systems enabling application management by a caregiver for a caregivee.

BACKGROUND

The background description provided herein is for the purpose of generally presenting the context of the disclosure. Work of the presently named inventors, to the extent it is described in the background section, as well as aspects of the description that may not otherwise qualify as prior art at the time of filing, are neither expressly nor impliedly admitted as prior art against the present disclosure.

Enterprises, such as retailers and pharmacies, generally have mobile applications via which an individual can interact with the enterprise. An example mobile application, for instance, may enable a user to manage retail orders, an enterprise loyalty program, and prescriptions with the enterprise. However, many individuals are unable to interact with the enterprise via such a mobile application due to difficulty utilizing the technology. In particular, individuals having impairments, such as those due to old age, disability, or illness, may be unable to navigate a mobile application designed for the general population, and thus may be unable to access all services and programs offered by the enterprise.

Such individuals (i.e., caregivees) may have caregivers that assist them with tasks during their daily lives. A caregiver may be able to operate an application for the caregivee, or interact with the enterprise on behalf of a caregivee for a specific purpose, such as filling a prescription. However, the caregiver is generally unable to manage all aspects of the caregivee's interactions with the enterprise (e.g., across all services, such as retail, pharmacy, loyalty, etc.), absent physically operating the mobile application for the caregivee or logging onto the mobile application with the caregivee's credentials. Further, if the caregiver is not physically present for the caregivee, the caregivee is left unable to effectively operate the mobile application. Thus, options are not currently available that both (i) enable a caregiver to holistically manage a caregivee's interactions with an enterprise and (ii) enable caregivees themselves to more easily operate a mobile application of the enterprise.

SUMMARY

Generally speaking, the present disclosure provides technologies for application management by a caregiver. In accordance with one example aspect of the present disclosure, a method is provided for enabling a first user account of a first user to manage a second user account of a second user, the first and the second user accounts associated with an enterprise. The method may be performed by one or more processors of a server associated with the enterprise. The method includes receiving, from a first computing device, via a first instance of an application at the first computing device, a request from the first user account for caregiver access to the second user account; verifying that the first user account is authorized by the second user account to receive the caregiver access; in response to the verifying, retrieving (i) account data of the second user account including prescription information indicating a prescription of the second user, and (ii) an application configuration including settings of the application for the second user account, the settings including notification settings for the prescription; providing the first user account with the caregiver access by providing access to the account data and the application configuration via the first instance of the application; receiving, from the first computing device, an update to the application configuration; and modifying the application configuration in accordance with the update.

In accordance with another exemplary aspect of the present disclosure, a server is provided including one or more processors, a non-transitory computer-readable medium, and instructions stored on the computer-readable medium. The instructions, when implemented by the one or more processors, cause the server to receive, from a first computing device, via a first instance of an application at the first computing device, a request from the first user account for caregiver access to the second user account; verify that the first user account is authorized by the second user account to receive the caregiver access; in response to the verifying, retrieve (i) account data of the second user account including prescription information indicating a prescription of the second user, and (ii) an application configuration including settings of the application for the second user account, the settings including notification settings for the prescription; provide the first user account with the caregiver access by providing access to the account data and the application configuration via the first instance of the application; receive, from the first computing device, an update to the application configuration; and modify the application configuration in accordance with the update.

In various embodiments, the notification settings include a notification sound for a reminder to consume the prescription. In such embodiments, receiving the update may include receiving an audio recording from the first computing device for use as the notification sound. In some embodiments, the notification settings include text for a reminder to consume the prescription.

In some embodiments, the method also includes, after modifying the application configuration, transmitting, to a second computing device associated with the second user, an indication causing a second instance of the application at the second computing device to present a notification in accordance with the notification settings.

Further, in some embodiments, the application configuration includes graphical user interface settings of a graphical user interface of the application. The update therefore may include a modification to the graphical user interface settings. The graphical user interface settings may include a layout of the graphical user interface. In addition, the method may include causing the first instance of the application to display a preview of the graphical user interface for the application in accordance with the graphical user interface settings. Such a preview may include one or more user-selectable options for modifying the graphical user interface settings, and receiving the modification to the graphical user interface settings may include receiving a selection of the one or more user-selectable options. Still further, the method may include, after modifying the application configuration, receiving an indication that the second user launched a second instance of the application at a second computing device; in response to receiving the indication, retrieving the application configuration; and transmitting the application configuration to the second computing device to cause the second instance of the application to display the graphical user interface in accordance with the graphical user interface settings.

Still further, in some embodiments, the update is a first update, and the method also includes receiving a second update to the account data from the first computing device and modifying the account data in accordance with the second update. The second update may correspond to a healthcare appointment for the second user, a retail order for the second user, a contact information update for the second user, or the prescription for the second user.

BRIEF DESCRIPTION OF THE DRAWINGS

The Figures described below depict various aspects of the system and methods disclosed therein. It should be understood that each figure depicts an example of a particular aspect of the disclosed system and methods, and that each of the figures is intended to accord with a possible example thereof. Further, wherever possible, the following description refers to the reference numerals included in the following figures, in which features depicted in multiple figures are designated with consistent reference numerals.

There are shown in the drawing arrangements which are presently discussed, it being understood, however, that the present examples are not limited to the precise arrangements and instrumentalities shown, wherein:

FIG. 3B is an example GUI of the application implemented on a caregiver device, the GUI including a preview of a GUI as it will appear for the caregivee user account;

FIG. 3C is an example GUI of the application implemented on a caregivee device, the GUI corresponding to the GUI previewed in FIG. 3B.

DETAILED DESCRIPTION

Overview

The present application provides systems and methods for a first user to manage a second user's account with an enterprise. More particularly, the disclosed techniques provide for caregiver management of a caregivee's (i) account data and (ii) configuration settings of an application of the enterprise, such that the caregiver can customize the way in which the caregivee digitally interacts with an enterprise.

In accordance with the techniques of this disclosure, a first user account associated with a first user (i.e., a caregiver) can be granted caregiver access to a second user account associated with a second user (i.e., a caregivee). If the first user account accesses an instance of an application of an enterprise at a first computing device, and the first user account is designated as a caregiver for the second user account, then the first user account can view and modify, via the application, account data for the second user account.

For example, a caregiver can manage a loyalty account of the caregivee, place retail or photo orders for the caregivee, manage prescriptions of the caregivee, make healthcare appointments for the caregivee, and otherwise manage any services of the enterprise via the application. The caregiver can also customize aspects of enterprise services for the caregivee. For example, in the context of retail services, if the caregivee is allergic to a particular item, the caregiver can prevent the item from appearing in advertisements or inventory lists displayed to the caregivee. Additional examples will be discussed throughout this disclosure.

Moreover, the caregiver can customize the application configuration of the application for the caregivee. Said another way, the caregiver can change how the application will be displayed on a device of the caregivee and how the application will present notifications to the caregivee. Thus, in addition to managing the caregivee's account data, the caregiver can make the application function in a way that facilitates the caregivee's use of the application. By enabling a caregiver to simplify and personalize the application for the caregivee, the disclosed techniques allow a caregivee to more effectively utilize the features of the application.

Example Computing Environment

Figure 1:
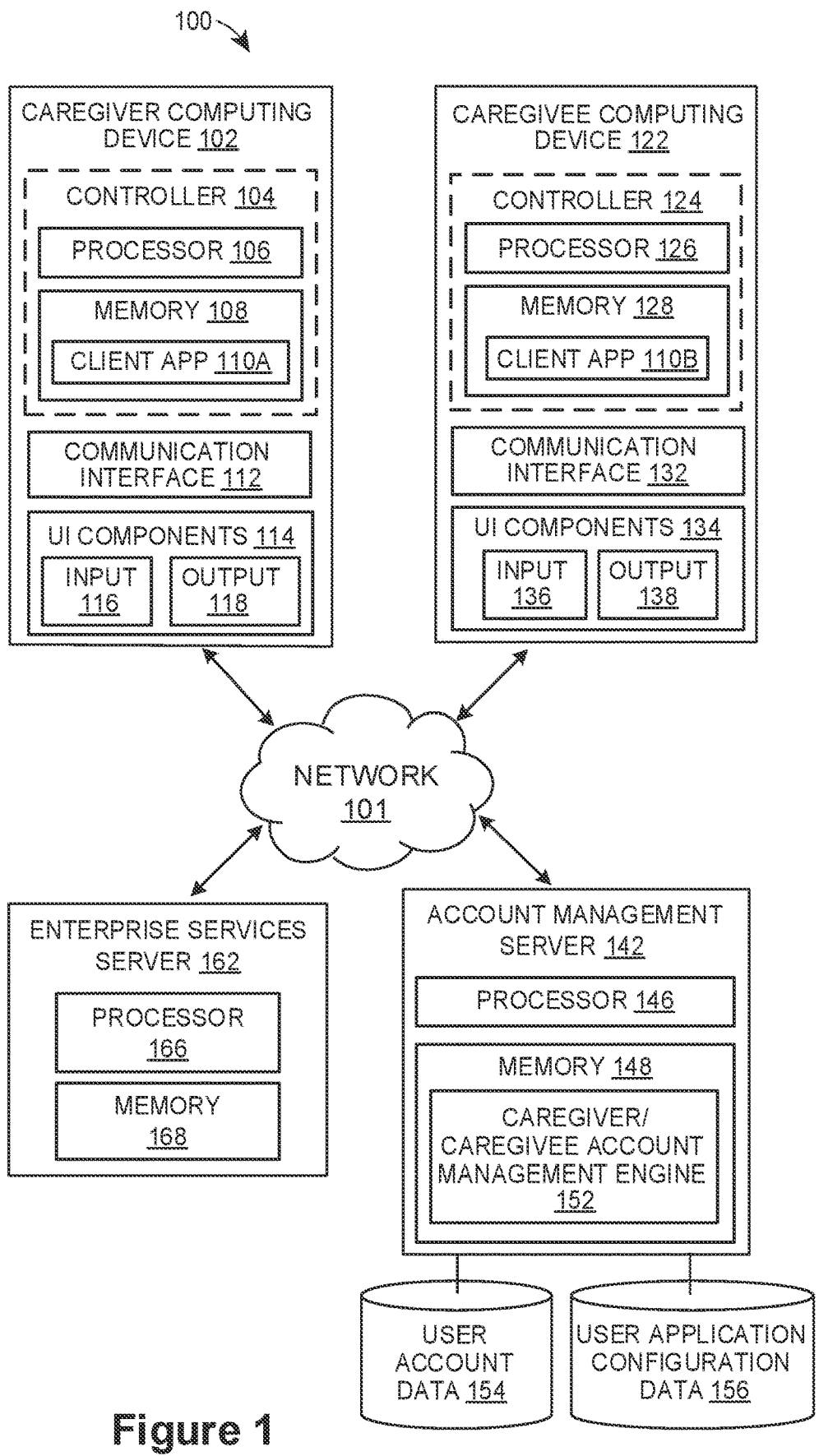
FIG. 1 is a block diagram of an example computing system in which techniques for application and account management can be implemented, in accordance with some embodiments.

FIG. 1 is a block diagram of an example computing system 100 in which the techniques of this disclosure for account and application management by a caregiver may be implemented. The system 100 includes several computing devices communicatively coupled via a network 101. The computing devices of the system 100 may include: a first computing device 102 associated with a first user, a second computing device 122 associated with a second user, an account management server 142, and at least one enterprise services server 162. The servers 142 and 162 may be associated with an enterprise, such as a vendor, retailer, merchant, pharmacy, or other business entity which provides goods and/or services to customers. Depending on the implementation, for example, one or more enterprise services server 162 and/or the account management server 142 may be owned and/or operated by the enterprise, or may be operated by a third-party entity on behalf of the enterprise.

The first and second users may have a first user account and a second user account, respectively, with the enterprise. In the examples discussed in this disclosure, the first user is an individual to which the second user grants access to the second user's account. Generally speaking, the first user is a caregiver for a caregivee corresponding to the second user, where a caregiver is an individual that assists the caregivee in their activities. The caregiver may have a formal caregiver role, such as a professional caregiver hired by the caregivee, or may be an informal caregiver for the caregivee, such as a family member or friend. The access that a caregivee grants to a caregiver is sometimes referred to in this disclosure as "caregiver access," where the caregiver access corresponds to access to both (i) account data, and (ii) an application configuration, of the caregivee. The manner in which a first user gains caregiver access to a second user account is described with reference to FIG. 2. Throughout this disclosure, the "first user" may interchangeably be referred to as the "caregiver," and the "second user" may interchangeably be referred to as the "caregivee."

The network 101 in general can include one or more wired and/or wireless communication links and may be a proprietary network, a secure public internet, a virtual private network, or some other type of network, such as dedicated access lines, telephone lines, satellite links, cellular data networks, combinations of these, etc. Where the network 101 comprises the Internet, data communications may take place over the network 101 via an Internet communication protocol.

The first computing device 102, which is also referred to herein as the caregiver computing device 102, is a computing device such as a mobile phone, tablet, laptop, desktop, etc.). The caregiver computing device 102 may include: (i) a controller 104 including one or more processor(s) 106 and a memory 108 coupled to the processor(s) 106 (e.g., via a bus—not shown), where the memory 108 can store machine-readable instructions executable on the processor(s) 106; (ii) a communication interface 112 coupled to the controller 104 (e.g., via the bus) and configured to enable communications via the network 101; and (iii) a set of user interface (UI) components 114 coupled to the controller 104 (e.g., via the bus), including one or more input UI components 116 and one or more output UI components 118. The caregiver computing device 102 may also include components not shown in FIG. 1.

The processor(s) 106 can include one or more general-purpose processors (e.g., central processing units (CPU(s)) or special-purpose processor units capable of executing machine-readable instructions stored on the memory 108. The memory 108 may be a non-transitory memory and may include one or several suitable memory modules, such as random access memory (RAM), read-only memory (ROM), flash memory, other types of persistent memory, etc. The communication interface 112 may include one or more transceivers (e.g., WWAN, WLAN, and/or WPAN transceivers) functioning in accordance with IEEE standards, 3GPP standards, or other suitable communication standards, and configured to receive and transmit data via one or more external ports. The one or more output UI components 118 may include an electronic display (e.g., an LCD display or other type of display screen), and the one or more input UI components 116 may include a keyboard, touch sensors integrated within the output UI components 118 (e.g., within an electronic display), or any other suitable input device for detecting user input. A user may interact with the one or more input UI components 116 to provide inputs to the caregiver computing device 102, and to perceive outputs of the caregiver computing device 102. The components of the first computing device 102 may be disposed within or throughout a housing of the first computing device 102.

Further, the caregiver computing device 102 implements a client application 110A, which may be stored as executable instructions on the memory 108. The client application 110A may be associated with the enterprise and may be operable by the first user of the caregiver computing device 102 to access the services of the enterprise and manage the account of a caregivee, in accordance with the techniques of this disclosure. The client application 110A, for example, may be a mobile application. The first user of the caregiver computing device 102 can interact with (i.e., both provide inputs to and perceive outputs of) the client application 110 via the input UI component(s) 116 and the output UI component(s) 118. For example, the client application 110A may implement graphical user interfaces (GUIs) that the caregiver computing device 102 can display via the output UI component(s) 118 and the first user can interact with via the input UI component(s) 116.

The client application 110A may have different modes depending on whether the first user of the caregiver computing device 102 is operating the client application 110A to manage their own account, or to manage the account or application settings of a second user. For example, the client application 110A may present user-selectable options for switching between a first profile, i.e., the first user's own profile, and a second profile, i.e., the first user's caregiver profile. When operating under the first profile, the client application 110A may present user-selectable options for viewing and modifying the first user's account and application settings. When operating under the second profile, the client application 110A may present user-selectable options for viewing and modifying the second user's account and application settings, where the first user is a caregiver for the second user, the caregivee. In order to switch to the second profile, the first user account receives approval from the second user account, as will be discussed with reference to FIG. 2. The first user may be designated as a caregiver for multiple other accounts, and therefore may have options to switch between several different profiles each corresponding to a different caregivee.

The second computing device 122, which is also referred to herein as the caregivee computing device 122, is generally similar to the caregiver computing device 102. Accordingly, the caregivee computing device 122 may include a controller 124, one or more processor(s) 126, a memory 128, a communication interface 132, UI components 134, input UI components 136, and output UI components 138, which may be similar to the components 104, 106, 108, 112, 114, 116, and 118, respectively. The caregivee computing device 122 implements a client application 110B, which may be stored as executable instructions on the memory 128. The client application 110B may be the same application (referred to herein as client application 110) as the client application 110A, but implemented at the caregivee computing device 122 rather than the caregiver computing device 102. Thus, the client application 110A is a first instance of a client application 110 executed at the caregiver computing device 102 and the client application 110B is a second instance of the client application 110 executed at the caregivee computing device 122.

The account management server 142 includes one or more processor(s) 146 and a memory 148, which may be similar to the processor(s) 106 and the memory 108, respectively. The account management server 142 may also include other components not shown in FIG. 1, such as a controller including the processor 146 and the memory 148, a communication interface, and UI components. The memory 148 implements a caregiver/caregivee account management engine 152, which may be stored as executable instructions on the memory 148. The caregiver/caregivee account management engine 152 is configured to implement the techniques of this disclosure for user account and application management. The components of the account management server 142 may be disposed within or throughout a housing of the account management server 142. In addition, Depending on the implementation, the described functionality provided by the account management server 142 may be provided by any suitable number of servers 142. That is, in some implementations, the account management server 142 may be implemented as a distributed system including, e.g., any desired number of computers, servers, databases, local or remote memories, etc.

To perform the techniques of this disclosure, the account management server 142 accesses user account data 154 and user application configuration data 156. The data 154 and 156 (or a portion of the data 154 and 156) may be stored in the memory 148, and/or may be stored in databases accessible by the account management server 142. While described separately, the data 154 and 156 may be stored in the same database, depending on the implementation. The user account data 154 includes account data for user accounts (e.g., the first user account associated with the first user, i.e., the caregiver, and the second user account associated with the second user, i.e., the caregivee) that users have with the enterprise. Example account data for a given user account includes, for example, a name, a username, a password or other data used to authenticate the user, contact information such as an email, phone number, and/or address, billing information such as a credit card number, caregiver or caregivee status (i.e., an indication of whether the account is associated with a caregiver or a caregivee, as will be described with more detail in reference to FIG. 2), and data related to services provided by the enterprise. For example, data related to services provided by the enterprise may include: order history, pending or current orders, favorite products/services and loyalty or rewards program information (e.g., reward points, coupons, discounts, etc.). An order may be for retail goods, or for services such as photography pick-up (e.g., if the enterprise prints photographs). Further, data related to services provided by the enterprise may include prescription information for the user (e.g., if the enterprise is a pharmacy). The prescription information may include information related to prescriptions of the user, such as current prescriptions, dosages, insurance information, prescribers, refill requests, automatic refill information, pharmacy location, delivery or pickup preferences, or other information/preferences related to prescriptions of the user. Still further, data related to services provided by the enterprise may include healthcare appointment information (e.g., if the enterprise provides healthcare or otherwise facilitates scheduling appointments with healthcare providers).

The user application configuration data 156 includes application configurations for the client application 110, where each user account may have a different application configuration. Accordingly, the user application configuration data 156 includes an application configuration associated with the caregiver user account and an application configuration associated with the caregivee user account. For example, when an instance of the client application 110 is launched at a particular computing device and a user logs into their user account, the application retrieves from the account management server 142 the application configuration for the user (e.g., by requesting the application configuration from the account management server 142) and configures itself in accordance with the application configuration. Continuing with this example, when the client application 110A launches on the caregiver computing device 102, the client application 110A configures itself in accordance with an application configuration for the caregiver user; when the client application 110B launches on the caregivee computing device 122, the client application 110B configures itself in accordance with an application configuration for the caregivee user.

An application configuration for the client application 110 includes settings for the client application 110, such as GUI layouts for one or more GUIs presented by the client application, notification types (e.g., push notifications displayed on a GUI, vibrations, sounds, or a combination), notification sounds, notification text, GUI colors, etc. A GUI layout, for example, may include which icons are displayed, the sizes of icons, icon label text, icon label sizes, menu locations, menu text, menu icons, which menu items are displayed, or other GUI element features or attributes.

The enterprise services server 162 includes one or more processor(s) 166 and a memory 168, which may be similar to the processor(s) 106 and the memory 108, respectively. The enterprise services server 162 may also include other components not shown in FIG. 1, such as a controller including the processor 166 and the memory 168, a communication interface, and UI components. The enterprise services server 162 may include multiple enterprise services servers 162. The enterprise may provide multiple services (e.g., retail orders, photography orders, pharmacy services, healthcare appointment scheduling, healthcare communications with healthcare providers, a loyalty program), where one or more enterprise services servers 162 support each service or a group of the multiple services. While not shown, the enterprise services server 162 may access/modify the user account data 154, similar to the account management server 142.

As mentioned above, each of the account management server 142 and the enterprise services server 162 may include multiple computing devices. Further, the functions of one or more of the servers 142 and 162 may be distributed among different computing devices, not only residing within a single machine, but deployed across a number of machines. For example, in some embodiments, one or more of the servers 142 and 162 may comprise multiple servers, which may comprise multiple, redundant, or replicated servers as part of a server farm. In some embodiments, one or more of the servers 142 and 162 may be implemented as cloud-based servers, such as a cloud-based computing platform. For example, one or more of the servers 142 and 162 may be any one or more cloud-based platform(s) such as MICROSOFT AZURE, AMAZON AWS, or the like.

Example Methods and Graphical User Interfaces

Figure 2:
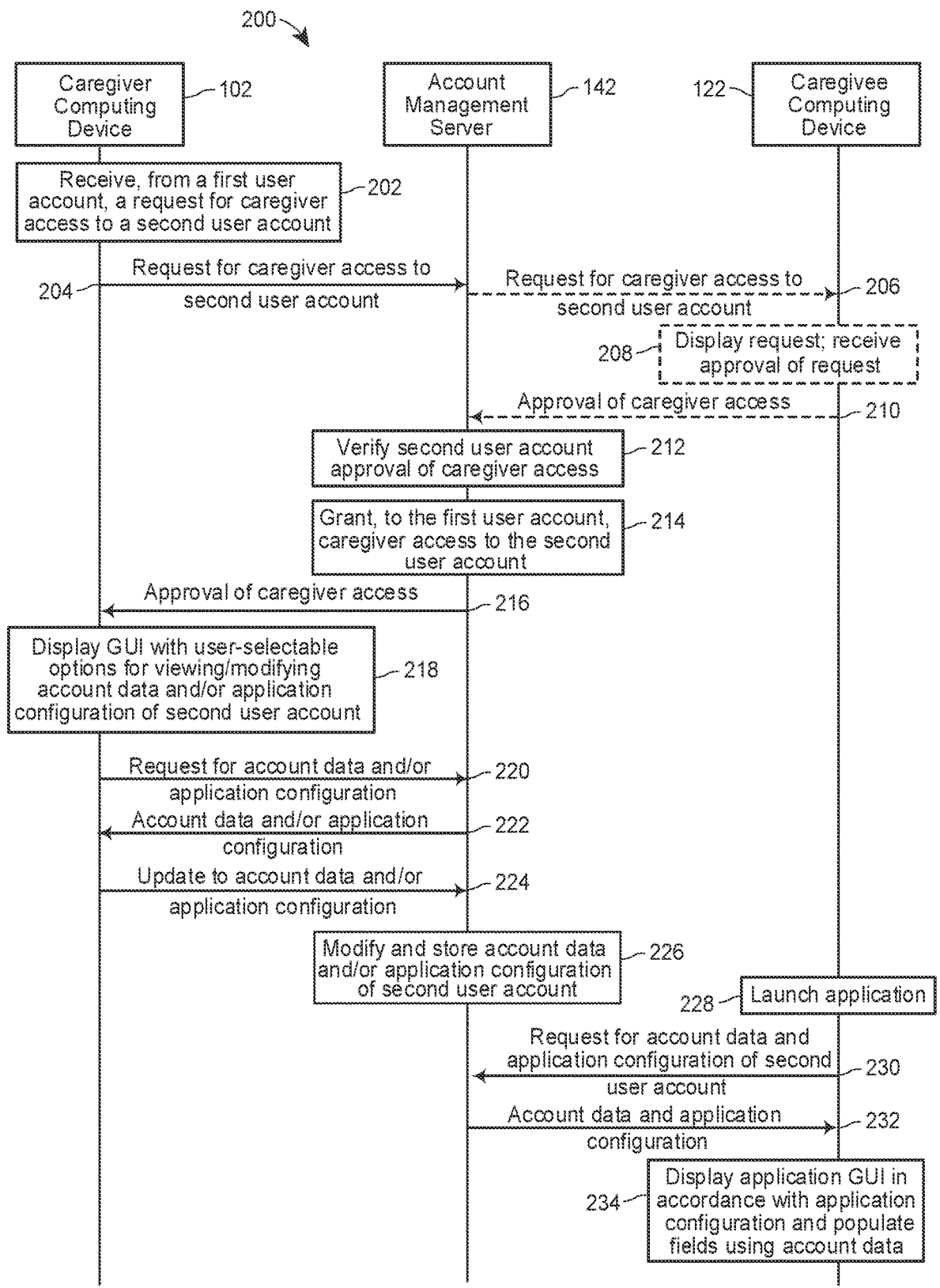
FIG. 2 is a messaging diagram of an example scenario in which an account management server enables a caregiver user account to modify account data and/or an application configuration for a caregivee user account, in accordance with some embodiments.

FIG. 2 illustrates an example messaging sequence implemented by components of the system 100 described above. It should be understood that FIG. 2 represents an example information flow, and that other information flows are also possible for other implementations. The functions of the caregiver computing device 102, the account management server 142, and the caregivee computing device 122 illustrated in FIG. 2 may be carried out by the client application 110A, the caregiver/caregivee account management engine 152, and the client application 110B, respectively.

Initially, the caregiver computing device 102 (or, more particularly, the client application 110A), receives 202, from a first user account, a request for caregiver access to a second user account. The first user account may or may not already be designated as a caregiver account for the second user account.

In a first instance, in which the first user account is not already designated as a caregiver account, a first user may launch the client application 110A using the caregiver computing device 102. The first user can then request, by interacting with the client application 110A, caregiver access to a second user account. The client application 110A, for example, can display user-selectable options that the first user can select to initiate the caregiver access request. For example, the user-selectable options may be to add a caregivee, or to switch from the first user's own profile (i.e., a first profile, as mentioned above) to a profile for managing a caregivee's account. If no caregivee is yet associated with the first user account, then the client application 110A can request the first user to designate a second user account for which the first user wishes to be a caregiver. The first user can designate the second user account by providing a name, username, email address, phone number, or other information identifying the second user account. The caregiver computing device 102 can then transmit 204, to the account management server 142, the request for caregiver access to the second user account. The account management server 142 (or, more particularly, the caregiver/caregivee account management engine 152) can then attempt to verify that the second user account has approved caregiver access for the first user account by accessing the user account data 154 for the first user account and/or the second user account.

If the first user account (and/or the second user account) does not indicate that the first user account is designated as a caregiver for the second user account, then the account management server 142 transmits 206, to the caregivee computing device 122, the request for caregiver access to the second user account. After receiving 206 the request, the caregivee computing device 122 (or, more particularly, the client application 110B) displays the request. For example, receiving 206 the request may prompt the client application 110B to display the request. The displayed request may indicate a name, username, or other identifying information of the first user such that the second user can identify the first user. The second user (i.e., the caregivee) can then interact with the client application 110B to provide approval of the request. For example, the displayed request may include user-selectable options to either deny or approve the request. After receiving 208 approval of the request, the caregivee computing device 122 transmits 210 an indication of the approval of the caregiver access. The account management server 142 can then verify 212 that the second user account has granted approval of the caregiver access. In response to verifying 212 the approval, the account management server 142 can modify the first user account data to designate that the first user account is a caregiver account for the second user account. Additionally or alternatively, the account management server 142 modifies the second user account data to designate that the second user account is a caregivee account, with the caregiver account being the first user account. For example, the account management server 142 can include a flag in the first user account data indicating that the first user is a caregiver for the second user, and/or include a flag in the second user account data indicating that the second user is a caregivee of the first user.

In a second instance, the first user account may already be designated as a caregiver account. The first user can launches the client application 110A and requests caregiver access to the second user account by interacting with the client application 110A. For example, the client application 110A can display a user-selectable option for switching from the first user's profile on the client application 110A to a second profile corresponding to the first user's caregiver profile for managing the second user account. After receiving 202 the request from the first user, the caregiver computing device 102 transmits the request to the account management server 142. In response, the account management server 142 can access the first user account data and/or the second user account data and automatically verify 212, without transmitting 206 the request to the caregivee computing device 122, that the second user account has already authorized the caregiver access. In some implementations, however, the account management server 142 may still transmit 206 the request in order to reauthorize the first user account as a caregiver. For example, the account management server 206 may transmit 206 the request if a predetermined amount of time (e.g., 1 week, 1 month, 1 year, etc.) has passed since the second user account previously approved caregiver access.

In granting 214, to the first user account, the caregiver access to the second user account, the account management server 142 gives the first user account (also referred to as the caregiver user account) permission to access and modify (i) user account data for the second user account and (ii) the application configuration for the second user account. In some implementations, when the caregiver computing device 122 receives 206 the request, the client application 110B can display user-selectable options to customize the level of caregiver access of the first user account. For example, the second user may indicate, via the client application 110B, that the first user account should be granted access only to user account data and not to the application configuration, or vice versa. As another example, the second user may indicate, via the client application 110B, that the first user can modify only certain aspects of the user account data or application configuration of the second user account. Thus, while full caregiver access includes access to all user account data and the application configuration of the second user account, the second user may customize the level of caregiver access. The examples of this disclosure primarily assume that the second user has granted full caregiver access. Further, the second user (i.e., the caregivee), after approving a request for caregiver access, can also withdraw the caregiver access from the first user account by interacting with the client application 110B. If the account management server 142 receives an indication from the caregivee computing device 122 that the caregiver access should be withdrawn, the account management server 142 can remove the caregiver designation from the first user account data and/or remove the caregivee designation from the second user account data, as necessary.

After granting 214 the caregiver access, the account management server 142 can transmit 216, to the caregiver computing device 102, an indication of approval by the second user account of the caregiver access.

In some embodiments, in addition to the caregiver-initiated request, or as an alternative option, the second user can request that the first user be designated as a caregiver for the second user. For example, the second user can interact with the client application 110B to request that the first user account be designated as a caregiver account for the second user account. The caregivee computing device 122 can transmit the request to the account management server 142. The account management server 142 can either automatically indicate in the first user account and/or the second user account that the first user account is a caregiver account for the second user account, or can first send an approval request to the first user account to verify that that the first user account accepts the role of caregiver prior to making the designation in the first user account and/or the second user account.

In any event, after or in response to receiving 216 the approval, the caregiver computing device 102, via the client application 110A, displays 218 a GUI with user-selectable options for viewing/modifying account data and/or the application configuration of the second user account. For example, after or in response to receiving 216 the approval, the client application 110A can switch from operating under the first user's own profile to the first user's caregiver profile for managing the account of the caregivee. This disclosure may refer to these two operating states as a "standard mode" and a "caregiver mode," respectively. An example GUI that the caregiver computing device 102 can display at event 218 is described below with reference to FIG. 3A.

By interacting with the client application 110A while the client application 110A operates in the caregiver mode, the first user can indicate user account data and/or application configuration settings that the first user would like to view or to modify. After receiving a selection of user account data or application configuration setting that the first user would like to view, the caregiver computing device 102 can transmit 220 a request for the selected account data or application configuration to the account management server 142. The account management server 142 can retrieve the requested information for the caregivee from the user account data 154 or user application configuration data 156, and transmit 222 the retrieved information to the caregiver computing device 102 for display by the client application 110A. The first user can then interact with the client application 110A to view or modify the user account data or application configuration of the caregivee. As the first user interacts with the client application 110A, the first user can continue to request user account data or application configuration settings of the caregivee, which the caregiver computing device 102 can request from the account management server 142.

The client application 110A can receive from the first user an update (i.e., a modification or change) to the account data or the application configuration. After receiving the update, the caregiver computing device 102 transmits 224 the update to the account management server 142. The account management server 142 can then modify 226 the account data and/or application configuration of the second user account in accordance with the update and store 226 the modified account data and/or application configuration. If the update is to the account data of the caregivee user account, then the account management server 142 modifies 226 the user account data 154. If the update is to the application configuration of the caregivee user account, then the account management server 142 modifies 226 the user application configuration data 156. Thus, the stored account data and application configuration for the caregivee user account are modified in accordance with updates received from the caregiver computing device 102.

At a later time, the caregivee computing device 122 launches the client application 110B (e.g., in response to receiving user input from the caregivee). The caregivee computing device 122 then requests 230 account data and the application configuration of the caregivee user account from the account management server 142 or otherwise indicates to the account management server 142 that the client application 110B is launching. In response, the account management server 142 transmits 232 to the caregivee computing device 122 the account data and application configuration to the caregivee computing device 122. The caregivee computing device 122 then configures the client application 110B in accordance with the received application configuration. The caregivee computing device 122 displays a GUI of the client application 110B formatted in accordance with the application configuration, and populates any user-specific fields with the account data for the second user. Accordingly, any updates made by the caregiver using the client application 110A are reflected in how the client application 110B operates and the information displayed by the client application 110B.

The account data, which the caregiver can view and modify at events 218-224, includes prescriptions information, loyalty program information, profile data, and information related to services offered by the enterprise, such as retail shopping, healthcare services, and photograph services.

With regard to prescription information, the caregiver can view and modify current prescriptions of the caregivee, order a refill for a prescription of the caregivee, transfer a prescription of the caregivee to a different pharmacy location, initiate a new prescription of the caregivee, set up a delivery of a prescription, set up a pick-up time for a prescription, or perform other actions related to prescriptions of the caregivee. After receiving a selection of an option for viewing prescriptions, for example, the client application 110A may display a list of current prescriptions, which can be further interacted with for more detailed information, such as prescription name, dosage, prescriber, refills remaining, delivery address, etc. Provided the caregivee has approved full caregiver access, the caregiver can view and manage all aspects of the caregivee's prescriptions by interacting with the client application 110A (e.g., by interacting with the GUI displayed at event 218). The caregiver can also manage prescription reminders, which is discussed in further detail below.

With regard to loyalty program information, the caregiver can view or redeem reward or loyalty points, discounts, promotions, and coupons of the caregivee, and otherwise manage aspects of the caregivee's loyalty program. Further, if the caregivee has not yet enrolled in the loyalty program of the enterprise, the caregiver can enroll the caregivee user account in the loyalty program.

With regard to profile information, the caregiver can view and modify profile information of the caregivee, such as name, username, contact information (e.g., email address, phone number, address), billing information (e.g., credit card number), language preferences, etc. As one example, the caregiver can manage delivery addresses for the caregivee. For example, if the caregivee has multiple addresses, the caregiver can indicate which of the multiple addresses is an active delivery address for the caregivee (i.e., the address to which prescription or retail good deliveries should be made). The caregiver can also indicate dates at which a delivery address should be active. Accordingly, if the caregivee maintains seasonal addresses (e.g., a first address during the winter and a second address during the summer), the caregiver can select the appropriate address for the corresponding time. As mentioned above, if the caregivee does not want to allow the caregiver to view or to edit such profile information, when responding to the request for caregiver access, the caregivee can deny the caregiver permission to view or edit some or all profile information.

If the enterprise offers retail shopping services, the account data can also include shopping information related to the caregivee user account. The caregiver can browse a product catalog on behalf of the caregivee, order retail goods for the caregivee, create shopping lists for the caregivee, favorite items, etc. Further, the caregiver can also customize the shopping experience of the caregivee. For example, the caregiver can hide items from the product catalog of the enterprise (e.g., because the caregivee is allergic to the items). When the caregivee later accesses the product catalog via the client application 110B, the hidden items will not be shown by the client application 110B. The caregiver can also select items that should be made more prominent for the caregivee or include certain items in a favorites list for the caregivee. When the caregivee later access the client application 110B, such items may be displayed at the top of the product catalog, or highlighted as favorite items. The caregiver can also edit the product catalog such that only favorited items are displayed to the caregivee, in order to simplify the shopping experience of the caregivee. Accordingly, the caregiver can customize which items are displayed to the caregivee and how such items are displayed (e.g., in what order items should be displayed).

If the enterprise offers photography services (e.g., services for printing photographs or photography projects), the account data can also include photography services information. The caregiver can view and modify stored photographs of the caregivee, order photograph prints or other photograph projects, check the status of a photograph order, or otherwise manage aspects of the caregivee's photographs.

If the enterprise offers healthcare services (e.g., in addition to prescription services), the account data can also include healthcare services information. For example, the enterprise may have a health goals program including health challenges that a user can complete in order to improve their health (e.g., exercise, healthy eating, and lifestyle challenges). The user can manually indicate completion of a health challenge, or a health challenge can automatically be tracked using a device such as a fitness tracker. Accordingly, the caregiver can configure such a health care program for the caregivee by, for example, enrolling the caregivee in the health goal program, selecting the health goal, inputting challenge completion data, and managing rewards earned as a result of meeting health goals. For instance, such a health goals program may be part of the loyalty program of the enterprise, such that the caregivee earns rewards for meeting health challenges. The health goals program information may be included in the healthcare services information.

Healthcare services information may also include information related to scheduling healthcare appointments and connecting with healthcare providers. For example, the caregiver can schedule in-person or virtual healthcare appointments with a healthcare provider on behalf of the caregivee, schedule vaccinations, enroll in clinical trials, or enroll in healthcare-related programs, such as exercise or nutrition plans. By enabling the caregiver to manage healthcare services information via the client application 110A, the disclosed techniques allow the caregivee to receive the benefits of the healthcare services provided by the enterprise without navigating the client application 110B.

Further, the application configuration for the caregiver user account, which the caregiver can view and modify at events 218-224 includes settings for the client application 110B, i.e., how the client application 110B will appear and function as implemented by the caregivee computing device 122.

The application configuration may include notification settings for the client application 110B. The caregiver can customize whether notifications, such as push notifications, are presented by the client application 110B for different events (e.g., notifications when retail orders/prescriptions/photography orders have been shipped, delivered, or are ready for pickup, prescription refill reminders, reminders to consume prescriptions, reminders for healthcare appointments, reminders to participate in health challenges, loyalty program notifications when rewards/discounts are available, retail notifications for sales, or other notifications presented by the client application 110B). The caregiver can also configure sounds, vibrations, and text displayed for the notifications. To configure notification sounds, the caregiver can select from a default list of sounds, select an audio recording stored on the caregiver computing device 102, or record a sound using the caregiver computing device 102 and select the recorded sound.

For example, the application configuration includes notification settings for reminders to consume a prescription (e.g., to apply a topical prescription or take an oral prescription), referred to herein as prescription reminders. The caregiver can edit whether the client application 110B should present prescription reminders for each prescription, and, if a prescription reminder is active, the notification settings for the prescription reminder. Such notification settings can include timing for the prescription reminders, the sound emitted by the caregivee computing device 122 (if any), the text of the notification (e.g., "Time to take pill X Grandpa!"), the color of the notification, etc. For instance, the caregiver can record themselves reciting a reminder for the prescription reminder (e.g., "Hi Grandpa! Remember to take your pill!"), and set the recording as the sound for the prescription reminder. Thus, for each prescription, the caregiver can customize the prescription reminders that the client application 110B will display or present to the caregivee.

The application configuration also may include GUI layout settings for one or more GUIs of the client application 110B. A GUI layout, for example, may include which icons are displayed, the sizes of icons, icon label text, icon label sizes, menu locations, menu text, menu icons, which menu items are displayed, GUI colors, or other GUI element features or attributes. The caregiver can select which icons will be displayed by a home screen GUI of the client application 110B when the client application 110B launches on the caregivee computing device 122, and the placement of the icons. For example, to simplify the home screen GUI for the caregivee, the caregiver can remove icons from the home screen GUI, or place icons lower on the home screen GUI. The caregiver can also customize the text of the home screen GUI. For example, the caregiver can change the label for an icon to access prescription information from "prescriptions" to "Your RX." The caregiver can also change the format for the home screen GUI. For example, instead of appearing as drop-down menus or list views, options on the home screen GUI can appear as separate icons. Further, the caregiver may change the font size for the labels for these icons, or the images displayed for different icons. While the examples of this disclosure primarily refer to a home screen GUI, the caregiver can change the layout of other GUIs of the client application 110B, such as GUIs for managing prescriptions, shopping, healthcare, photography services, or other services within the client application 110B.

As will be discussed in further detail with reference to FIGS. 3B-3C, the caregiver can also interact with the client application 110A to view a preview of a GUI as it will appear on the caregivee computing device 122 in accordance with the application configuration. The preview may include user-selectable options for editing the GUI elements.

The client application 110 can also support chat functions between the caregiver and the caregivee. For example, when operating in caregiver mode, the client application 110A may display user-selectable options for initiating a communication with the caregivee (e.g., an audio call, text message, or chat). After the client application 110B is launched on the caregivee computing device 122, the client application 110B may display user-selectable options for initiating a communication with the caregiver (e.g., an audio call, text message, or chat).

Figure 3A:
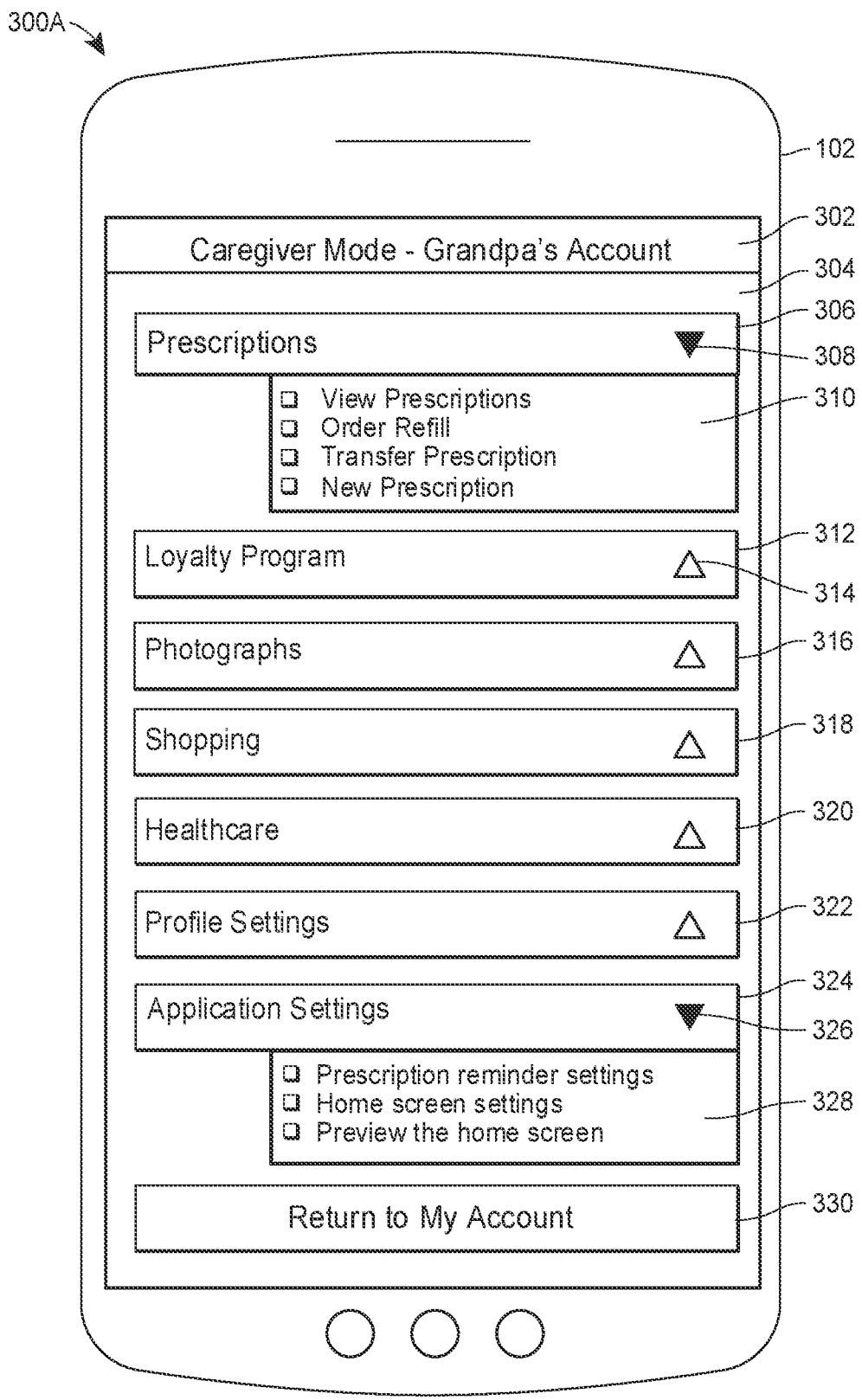
FIG. 3A is an example graphical user interface (GUI) of an application implemented on a caregiver device, the GUI for managing account data and/or an application configuration, in accordance with some embodiments.

Additional examples of the account data and application configuration settings that the caregiver can view and modify are discussed next using the example GUIs in FIGS. 3A-3C. It should be understood that the GUIs illustrated in FIGS. 3A-3C are example GUIs illustrated for the purpose of describing the functionality of the client application 110, and that other GUI layouts enabling the functionality described by this disclosure are also contemplated. Further, it should also be understood that other example GUIs may include options different from or in addition to those illustrated in FIGS. 3A-3C.

FIG. 3A illustrates an example GUI 300A that the caregiver computing device 102 can display at event 218. The example GUI 300A of the client application 110A can be displayed by a display screen 304 (e.g., belonging to the UI components 114) of the caregiver computing device 102. The example GUI 300A is displayed by the client application 110A when the client application 110A operates in the caregiver mode. The GUI 300A includes an information element 302 indicating that the client application 110A is operating in the caregiver mode and that the first user is viewing options related to a caregivee. The information element 302 may include an indicator of the caregivee-such as their name, username, or a customized name, "Grandpa" in the example of FIG. 3A. The first user can set up the customized name by interacting with the client application 110A. The GUI 300A also includes a user-selectable option 330 for returning to standard mode, i.e., for switching back to the first profile.

Generally speaking, the GUI 300A includes user-selectable options for viewing and modifying the account data and application configuration of the caregivee user account. The GUI 300A includes a prescription menu 306, where drop-down menu options related to prescriptions are displayed after the client application 110A receives a selection of the drop-down arrow 308. FIG. 3A shows the drop-arrow 308 in a selected state, such that the sub-menu 310 including user-selectable options related to prescriptions are displayed, such as viewing the prescriptions of the caregivee, ordering a refill for the caregivee, transferring a caregivee's prescription to another pharmacy, and ordering a new prescription. Thus, by interacting with the prescription menu 306 and sub-menu 310, the caregiver can view and modify the prescription information of the caregivee. Other menus that the GUI 300A can display include a loyalty program menu 312 (which can include an unselected drop-down arrow 314), a photograph menu 316, a shopping menu 318, a healthcare menu 320, a profile settings menu 322, and an application settings menu 324. By interacting with these respective menus, the caregiver can view and modify loyalty program information, photography services information, shopping information, healthcare services information, shopping information, profile information, and the application configuration for the caregivee user account.

The application settings menu 324, for example, can include a drop-down arrow 326. After the client application 110A receives a selection of the drop-down arrow 326, the sub-menu 328 is displayed including options related to viewing and modifying the application configuration of the caregivee user account. For example, such options can include editing prescription reminder settings, editing home screen settings (e.g., the appearance of a home screen GUI of the client application 110B), and previewing a home screen of the caregivee. Prescription reminder settings may also be accessible via the prescription menu 306. If the client application 110A receives a selection of the prescription reminder settings option, the client application 110A can display user-selectable options related to viewing and changing the notification settings for prescription reminders. If the client application 110A receives a selection of the home screen settings option, the client application 110A can display user-selectable options related to viewing and changing home screen GUI settings for the caregivee user account. Further, if the client application 110A receives a selection of the preview option, the client application 110A can display a preview of the home screen GUI.

FIG. 3B illustrates an example GUI 300B, which may be displayed by the caregiver computing device 102 if the client application 110A receives a selection of the preview option. The example GUI 300B of the client application 110A can be displayed by the display screen 304 of the caregiver computing device 102. The GUI 300B may include an information element 332 indicating that the caregiver is viewing a preview of the caregivee's screen, and the caregiver may select the information element 332 to return back to the caregiver's view of the client application 110A. The GUI 300B is a preview of the home screen GUI that the client application 110B will display upon launch. The caregiver can customize the GUI 300B such that the GUI 300B can be effectively utilized by the caregivee. That is, the caregiver can personalize the GUI 300B for the needs of the caregivee. If the caregivee has vision difficulties, for example, the caregiver can increase the size of the icon labels. If the caregivee utilizes certain functions more than others, the caregiver can move these functions to be higher on the GUI 300B such that they are more easily accessible to the caregivee.

The GUI 300B may include a notification center 336 displaying personalized reminders, to-do items, or messages for the caregivee. The caregiver can configure the notification center 336 by interacting with an edit tool 338. After receiving a selection of the edit tool 338, the client application 110A can display user-selectable options for configuring which events (e.g., prescription pickup times, prescription reminders, retail/photograph/prescription order statuses and delivery times, etc.) populate the notification center 336, and for customizing the text that appears in the notification center 336.

The GUI 300B may include icons, depending on the customized layout configured by the caregiver. The caregiver can edit the overall layout of the GUI 300B by interacting with an edit tool 350, for example. The icons may include a prescription icon 340, a photograph services icon 342, an appointments icon 346, and a chat icon 348, each of which may include an edit tool, such as the edit tool 344 for the photograph services icon 342. In the example of FIG. 3B, the caregiver has selected prescriptions, photographs, appointments (i.e., healthcare appointments, configured by editing healthcare services information), and chat, to represented on the visible portion of the GUI 300B. However, the caregiver can select any one or more of the functionalities of the client application 110B to appear on the GUI 300B, depending on the needs of the caregivee. Further, by interacting with the edit tool (e.g., the edit tool 344) for each icon, the caregiver can customize the label, font size, icon size, and placement of the icon. For example, a default label for activating a chat functionality of the client application 110B may be "Chat," but the caregiver can edit the label of the chat icon 348 to be "Chat with Steve," where Steve is the caregiver's name. The chat icon 348 is therefore personalized for the caregivee.

After the caregiver configures the GUI 300B, the changes to the application configuration are transmitted (e.g., event 224) to the account management server 142. When the caregivee computing device 122 launches the client application 110B, the home screen GUI that the caregivee computing device 122 displays (e.g., at event 234) is a GUI 300C, illustrated in FIG. 3C. The example GUI 300C of the client application 110B can be displayed by a display screen 354 (e.g., of the UI components 134) of the caregivee computing device 122. The caregivee computing device 122 displays the GUI 300C in accordance with the application configuration, and therefore the GUI 300C matches the preview illustrated in the GUI 300B, with the exception that the GUI 300C does not include edit tools (e.g., the edit tools 338, 344, and 350). Accordingly, the GUI 300C includes a notification center 356, prescription icon 360, photograph services icon 362, appointments icon 366, and chat icon 368, which the caregivee can interact with in order to view/access their prescription information, view/access their photograph services information, view/access their appointments, and initiate a chat, respectively. If the caregivee wishes to edit the application configuration, the caregivee can still do so by interacting with the client application 110B to change the application configuration settings. More generally, the caregivee retains the ability to manage their account data and application configuration, even if the caregivee is associated with a caregiver. Further, the GUI 300C may include an information element 370 indicating that the caregivee's account is being managed by a caregiver, which the caregivee can interact with in order to change the access level of the caregiver.

Figure 4:
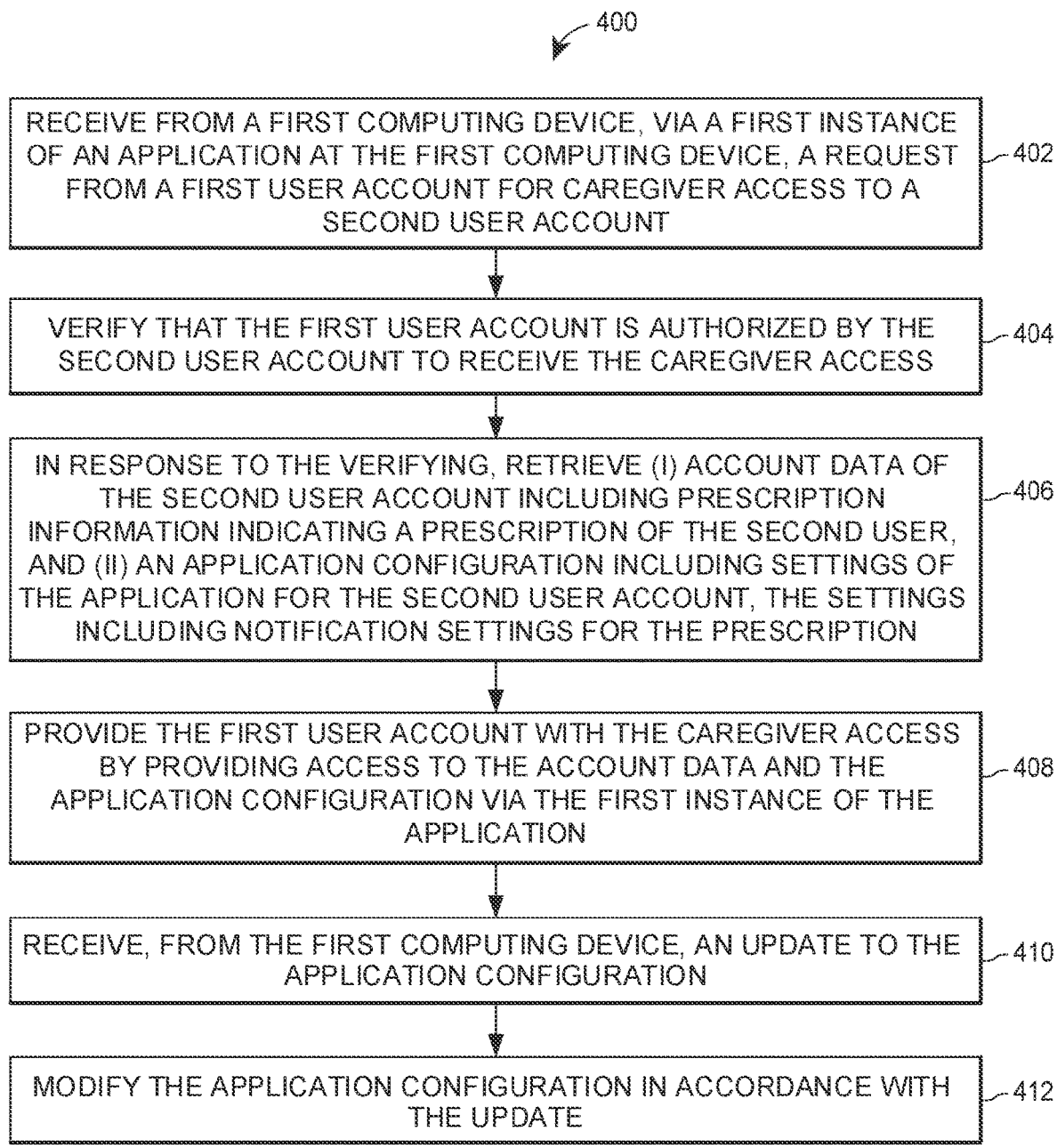
FIG. 4 is a flow diagram of an example method for enabling a first user account of a first user to manage a second user account of a second user, in accordance with some embodiments.

FIG. 4 is a flow diagram of an example method 400 for enabling a first user account of a first user (e.g., a caregiver) to manage a second user account of a second user (e.g., a caregivee), the first and second user accounts associated with an enterprise. The method 400 may be implemented by one or more processors of a server associated with the enterprise (e.g., the one or more processor(s) 146 of the account management server 142). The server can implement the method 400 as a set of instructions stored on a non-transitory computer-readable memory (e.g., the memory 148) and executable by the one or more processors.

At block 402, the server receives, from a first computing device (e.g., the caregiver computing device 102), via a first instance of an application at the first computing device (e.g., the client application 110A), a request from a first user account for caregiver access to a second user account (e.g., event 204). At block 404, the server verifies that the first user account is authorized by the second user account to receive the caregiver access (e.g., event 212). For example, the server can transmit a request to the second user to request approval, or can verify whether the first user account is designated as a caregiver for the second user account based on account data for the first and/or second user account At block 406, in response to the verifying, the server retrieves (i) account data of the second user account including prescription information indicating a prescription of the second user, and (ii) an application configuration including settings of the application for the second user account, the settings including notification settings for the prescription. The notification settings, for example, may include a notification sound for a reminder to consume the prescription. As another example, the notification settings may include text for a reminder to consume the prescription. The application configuration may further include GUI settings of at least one GUI of the application. The GUI settings may include a layout of the at least one GUI.

At block 408, the server provides the first user account with the caregiver access by providing access to the account data and the application configuration via the first instance of the application (e.g., events 214, 216, 222). To provide the caregiver access, the server grants permissions to the first user account to access the account data and the application configuration. The server also causes the first instance of the application to display GUIs that enable the first user to interact with the first instance of the application to view and modify the account data and the application configuration. For example, providing the first user account with the caregiver access may include causing the first instance of the application to display a preview of the GUI for the application in accordance with the GUI settings (e.g., the GUI 300B). The preview may include one or more user-selectable options for modifying the GUI settings.

At block 410, the server receives, from the first computing device, an update to the application configuration (e.g., event 224). For example, if the update is to a notification sound, receiving the update may include receiving an audio recording from the first computing device for use as the notification sound. As another example, if the update is to GUI settings of a GUI of the application, then receiving the update may include receiving a modification to the GUI settings. As a further example, receiving the modification to the GUI settings may include receiving a selection of one or more user-selectable options included in a preview of a GUI.

At block 412, the server modifies the application configuration in accordance with the update (e.g., event 226). In some implementations, after modifying the application configuration, the server may transmit, to a second computing device (e.g., the caregivee computing device 122) associated with the second user, an indication causing a second instance of the application (e.g., the client application 110B) to present a notification in accordance with the notification settings. For example, the server may push the modified application configuration to the second computing device, and the second instance of the application can configure itself in accordance with the notification settings. As another example, the second instance of the application can, upon launch, retrieve a stored application configuration from the server and configure itself in accordance with the notification settings.

In some implementations, after modifying the application configuration, the server may receive an indication that the second user launched the second instance of the application at the second computing device. In response, the server can retrieve the application configuration and transmit the application configuration to the second computing device to cause the second instance of the application to display the GUI in accordance with the GUI settings. In some implementations, after modifying the application configuration, the server may instead push the application configuration to the second instance of the application without receiving a request. In such implementations, the second instance of the application displays the GUI in accordance with the GUI settings upon launch.

In various implementations, the update to the application configuration may be a first update. The method 400 may further include receiving, from the first computing device, a second update to the account data. The server can then modify the account data in accordance with the second update. The second update may correspond to, for example, a healthcare appointment, a retail order, a contact information update, or a prescription for the second user.

Additional Considerations

Although the following text sets forth a detailed description of numerous different embodiments, it should be understood that the legal scope of the invention may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A method for enabling a first user account of a first user to manage a second user account of a second user, the first user account and the second user account associated with an enterprise, the method comprising:
   receiving, at one or more processors of a server associated with the enterprise from a first computing device, via a first instance of an application at the first computing device, a request from the first user account for caregiver access to the second user account;
   verifying, by the one or more processors, that the first user account is authorized by the second user account to receive the caregiver access;
   in response to the verifying, retrieving, by the one or more processors, (i) account data of the second user account including prescription information indicating a prescription of the second user, and (ii) an application configuration including settings of the application for the second user account, the settings including notification settings for the prescription and graphical user interface settings of a graphical user interface of the application for the second user account;
   providing, by the one or more processors, the first user account with the caregiver access by providing access to the account data and the application configuration via the first instance of the application;
   causing, by the one or more processors, the first instance of the application to display a preview of the graphical user interface for the application, via the first user account, in accordance with the graphical user interface settings for the second user account, the preview including one or more user-selectable options for modifying the graphical user interface settings;
   receiving, at the one or more processors from the first computing device, an update to the application configuration for the second user account, including a modification to the graphical user interface settings for the second user account, via a selection of the one or more user-selectable options;
   modifying, by the one or more processors, the application configuration in accordance with the update; and
   after modifying the application configuration, transmitting, by the one or more processors to a second computing device associated with the second user, an indication causing a second instance of the application at the second computing device to present a notification in accordance with the notification settings.

2. The method of claim 1, wherein the notification settings include a notification sound for a reminder to consume the prescription.

3. The method of claim 2, wherein receiving the update includes receiving an audio recording from the first computing device for use as the notification sound.

4. The method of claim 1, wherein the notification settings include text for a reminder to consume the prescription.

5. The method of claim 1, wherein the graphical user interface settings include a layout of the graphical user interface.

6. The method of claim 1, further comprising:
   after modifying the application configuration, receiving, at the one or more processors, an indication that the second user launched a second instance of the application at a second computing device;
   in response to receiving the indication, retrieving, by the one or more processors, the application configuration; and
   transmitting, by the one or more processors, the application configuration to the second computing device to cause the second instance of the application to display the graphical user interface in accordance with the graphical user interface settings.

7. The method of claim 1, wherein:
   the update is a first update, the method further comprising:
      receiving, at the one or more processors from the first computing device, a second update to the account data; and
      modifying, by the one or more processors, the account data in accordance with the second update.

8. The method of claim 7, wherein the second update corresponds to:
   a healthcare appointment for the second user;
   a retail order for the second user;
   a contact information update for the second user; or
   the prescription for the second user.

9. A server for enabling a first user account of a first user to manage a second user account of a second user, the first user account and the second user account associated with an enterprise, the server comprising:
   one or more processors;
   a non-transitory computer-readable medium; and
   instructions stored on the non-transitory computer-readable medium, wherein the instructions, when implemented by the one or more processors, cause the server to:
      receive, from a first computing device, via a first instance of an application at the first computing device, a request from the first user account for caregiver access to the second user account;
      verify that the first user account is authorized by the second user account to receive the caregiver access;
      in response to the verifying, retrieve (i) account data of the second user account including prescription information indicating a prescription of the second user, and (ii) an application configuration including settings of the application for the second user account, the settings including notification settings for the prescription and graphical user interface settings of a graphical user interface of the application for the second user account;
      provide the first user account with the caregiver access by providing access to the account data and the application configuration via the first instance of the application;

cause the first instance of the application to display a preview of the graphical user interface for the application, via the first user account, in accordance with the graphical user interface settings for the second user account, the preview including one or more user-selectable options for modifying the graphical user interface settings;

receive, from the first computing device, an update to the application configuration for the second user account, including a modification to the graphical user interface settings for the second user account, via a selection of the one or more user-selectable options;

modify the application configuration in accordance with the update; and after modifying the application configuration, transmit, to a second computing device associated with the second user, an indication causing a second instance of the application at the second computing device to present a notification in accordance with the notification settings.

10. The server of claim 9, wherein the notification settings include a notification sound for a reminder to consume the prescription.

11. The server of claim 10, wherein the update includes an audio recording from the first computing device for use as the notification sound.

12. The server of claim 9, wherein the notification settings include text for a reminder to consume the prescription.

13. The server of claim 9, wherein the instructions further cause the server to:

after modifying the application configuration, receive an indication that the second user launched a second instance of the application at a second computing device;

in response to receiving the indication, retrieve the application configuration; and transmit the application configuration to the second computing device to cause the second instance of the application to display the graphical user interface in accordance with the graphical user interface settings.

* * * * *